ed States Patent

(12) United States Patent
Ta et al.

(10) Patent No.: US 11,759,627 B2
(45) Date of Patent: Sep. 19, 2023

(54) WOUND-HEALING SYSTEMS AND METHODS THEREOF

(71) Applicant: Bard Access Systems, Inc., Salt Lake City, UT (US)

(72) Inventors: Teresa Ta, Murray, UT (US); Gidon Ofek, Millcreek, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 409 days.

(21) Appl. No.: 17/140,990

(22) Filed: Jan. 4, 2021

(65) Prior Publication Data

US 2021/0205611 A1 Jul. 8, 2021

Related U.S. Application Data

(60) Provisional application No. 62/956,897, filed on Jan. 3, 2020.

(51) Int. Cl.
*A61N 1/04* (2006.01)
*A61N 1/36* (2006.01)
(Continued)

(52) U.S. Cl.
CPC ...... *A61N 1/0468* (2013.01); *A61F 13/00063* (2013.01); *A61F 13/02* (2013.01);
(Continued)

(58) Field of Classification Search
CPC .. A61M 2025/0246; A61M 2025/0266; A61M 25/02; A61N 1/0468; A61N 1/0484; A61N 1/048; A61N 1/0492; A61N 1/04
See application file for complete search history.

(56) References Cited

U.S. PATENT DOCUMENTS 7,076,282 B2    7/2006  Munro et al.
7,989,674 B2    8/2011  Flick
(Continued)

FOREIGN PATENT DOCUMENTS

WO       9517923 A1     7/1995
WO    2010132843 A1    11/2010
(Continued)

OTHER PUBLICATIONS

PCT/US2021/012098 filed Jan. 4, 2021 International Search Report and Written Opinion dated Mar. 18, 2021.

*Primary Examiner* — Deanna K Hall
(74) *Attorney, Agent, or Firm* — Rutan & Tucker LLP

(57) ABSTRACT

Disclosed herein are wound-healing systems and methods thereof. A wound-healing system can include a wound dressing, a catheter-stabilization device, and an electrical-stimulation means for applying electrical stimulation to heal or protect at least a wound associated with a percutaneous insertion site of a patient. The wound dressing can be configured as an electrode for placement around the wound. The catheter-stabilization device can include an anchor pad and a retainer coupled to the anchor pad. The anchor pad can be configured to adhere to skin of the patient proximate the insertion site. The retainer can be configured to stabilize a catheter assembly while a catheter tube of the catheter assembly is disposed in the insertion site. The electrical-stimulation means can include an electrical power source and an external circuit between the catheter-stabilization device and the wound dressing for applying the electrical stimulation.

24 Claims, 3 Drawing Sheets

(51) Int. Cl.
*A61F 13/00* (2006.01)
*A61F 13/02* (2006.01)
*A61M 25/02* (2006.01)

(52) U.S. Cl.
CPC ........... *A61M 25/02* (2013.01); *A61N 1/0496* (2013.01); *A61N 1/36031* (2017.08); *A61M 2025/0246* (2013.01); *A61M 2025/0266* (2013.01)

(56) References Cited

U.S. PATENT DOCUMENTS

| | | |
|---|---|---|
| 10,201,703 B2 | 2/2019 | Bogie et al. |
| 2012/0130315 A1 | 5/2012 | Weadock et al. |

FOREIGN PATENT DOCUMENTS

| | | |
|---|---|---|
| WO | 2015187858 A1 | 12/2015 |
| WO | 2021/138675 A1 | 7/2021 |

WOUND-HEALING SYSTEMS AND METHODS THEREOF

PRIORITY

This application claims the benefit of priority to U.S. Provisional Application No. 62/956,897, filed Jan. 3, 2020, which is incorporated by reference in its entirety into this application.

BACKGROUND

Infectious microorganisms such as bacteria can invade a patient's body through a catheter tube disposed in a percutaneous insertion site and subsequently cause an infection (e.g., a deep-tissue infection, sepsis, etc.). While such microorganisms can invade the patient's body through a lumen of the catheter tube, it is more likely the microorganisms colonizing skin of the patient about the insertion site will invade the patient's body. Thus, clinicians routinely suppress the microorganisms about the insertion site by applying an antiseptic such as an alcohol-based chlorhexidine or iodopovidone solution prior to catheterization. However, the microorganisms rapidly grow back about the insertion site during the catheterization, thereby requiring frequent dressing changes in order to reapply the antiseptic and mitigate risk of infection. This leaves ample room for clinician error with respect to inadvertently missing a dressing change, missing or inappropriately applying the antiseptic during a dressing change, or the like.

Disclosed herein are wound-healing systems and methods thereof that address at least the foregoing.

SUMMARY

Disclosed herein is a wound-healing system including, in some embodiments, a wound dressing, a catheter-stabilization device, and an electrical-stimulation means for applying electrical stimulation to heal or protect at least a wound associated with a percutaneous insertion site of a patient. The wound dressing is configured as an electrode for placement around the wound. The catheter-stabilization device includes an anchor pad and a retainer coupled to the anchor pad. The anchor pad is configured to adhere to skin of the patient proximate the insertion site. The retainer is configured to stabilize a catheter assembly while a catheter tube of the catheter assembly is disposed in the insertion site. The electrical-stimulation means includes an electrical power source and an external circuit between the catheter-stabilization device and the wound dressing for applying the electrical stimulation.

In some embodiments, the wound-healing system further includes an adhesive bandage for placement over a combination of the wound dressing, the catheter-stabilization device, and the catheter assembly. The adhesive bandage is configured to adhere the combination of the wound dressing, the catheter-stabilization device, and the catheter assembly to the patient for further stabilization.

In some embodiments, the wound dressing includes an electrically conductive body. The body of the wound dressing includes a matrix of a naturally occurring polymer, a synthetic polymer, or a composite thereof having a metal, a salt, a conducting polymer, or a conducting allotrope of carbon dispersed therein.

In some embodiments, the body of the wound dressing includes an electrically conductive hydrogel.

In some embodiments, the wound dressing includes a body. The body of the wound dressing includes a matrix of a naturally occurring polymer, a synthetic polymer, or a composite thereof configured to become electrically conductive when at least partially saturated with a bodily fluid.

In some embodiments, the wound dressing includes an antimicrobial agent.

In some embodiments, the external circuit includes a pair of electrical leads extending from the catheter-stabilization device for connecting with the wound dressing. The electrical leads are constructed from coated metal wiring, electrically conductive paint, or a combination thereof.

In some embodiments, the electrical-stimulation means includes an integrated circuit disposed in a body of the retainer or a wing or cover of the retainer for locking a portion of the catheter assembly in the retainer. The integrated circuit includes at least a power circuit coupled to the external circuit configured to convey electrical power from the electrical power source to the wound dressing and a control circuit configured to modulate how the electrical power is delivered to the wound dressing.

In some embodiments, the integrated circuit is configured to modulate the electrical power such that a low-intensity current between about 200 and 1000 mA is continuously delivered to the wound dressing for more than 1 s at a time. The current has a particular polarity.

In some embodiments, the integrated circuit is configured to modulate the electrical power such that a high-voltage current between about 50 and 150 V is delivered to the wound dressing in 1-ms pulses. The current has an alternating polarity or a particular polarity.

In some embodiments, the integrated circuit includes biofeedback logic configured to detect changes in impedance through the skin of the patient or the wound dressing. The biofeedback logic is also configured to modulate how the electrical power is delivered to the wound dressing in accordance with the changes in impedance.

In some embodiments, the electrical power source is a battery. The battery is either rechargeable or replaceable.

In some embodiments, the battery is rechargeable. The retainer includes a port for charging the rechargeable battery.

In some embodiments, the retainer includes one or more light-emitting diodes ("LEDs") configured to indicate when the electrical-stimulation means is active.

In some embodiments, the wound-healing system further includes a controller configured to communicatively connect to the catheter-stabilization device and allow a user thereof to modulate how the electrical power is delivered to the wound dressing.

Also disclosed herein is a wound-healing system including, in some embodiments, a wound dressing, a catheter-stabilization device, an electrical-stimulation means for applying electrical stimulation to heal or protect at least a wound associated with a percutaneous insertion site of a patient, and an adhesive bandage. The wound dressing is configured as an electrode for placement around the wound. The catheter-stabilization device includes an anchor pad and a retainer coupled to the anchor pad. The anchor pad is configured to adhere to skin of the patient proximate the insertion site. The retainer is configured to stabilize a catheter assembly while a catheter tube of the catheter assembly is disposed in the insertion site. The electrical-stimulation means includes an electrical power source, an external circuit between the catheter-stabilization device and the wound dressing, and an integrated circuit disposed in a body of the retainer or a wing or cover of the retainer for locking a portion of the catheter assembly in the retainer.

The external circuit includes a pair of electrical leads extending from the catheter-stabilization device for connecting with the wound dressing and applying the electrical stimulation. The integrated circuit includes at least a power circuit and a control circuit. The power circuit is coupled to the external circuit and configured to convey electrical power from the electrical power source to the wound dressing. The control circuit is configured to modulate how the electrical power is delivered to the wound dressing. The adhesive bandage is configured for placement over a combination of the wound dressing, the catheter-stabilization device, and the catheter assembly to adhere the combination to the patient for further stabilization thereof.

Also disclosed herein is a method of a wound-healing system including, in some embodiments, a wound dressing-applying step of applying a wound dressing around a wound associated with a percutaneous insertion site of a patient. The wound dressing is configured as an electrode. The method also includes an adhering step of adhering an anchor pad of a catheter-stabilization device to skin of the patient proximate the insertion site. The method also includes a stabilizing step of stabilizing a catheter assembly in a retainer of the catheter-stabilization device. The retainer is coupled to the anchor pad. The method also includes an electrical stimulation-applying step of applying electrical stimulation with an electrical-stimulation means therefor to heal or protect the wound. The electrical-stimulation means includes an electrical power source and an external circuit between the catheter-stabilization device and the wound dressing for applying the electrical stimulation.

In some embodiments, the method further includes an inserting step of inserting a catheter tube of the catheter assembly into the insertion site before stabilizing the catheter assembly in a retainer of the catheter-stabilization device.

In some embodiments, the method further includes a placing step of placing an adhesive bandage over a combination of the wound dressing, the catheter-stabilization device, and the catheter assembly to adhere the combination to the patient for further stabilization.

In some embodiments, the method further includes an electrical lead-connecting step of connecting a pair of electrical leads from the catheter-stabilization device to the wound dressing to form an external circuit for applying the electrical stimulation.

In some embodiments, the electrical lead-connecting step includes painting the electrical leads on the catheter assembly with electrically conductive paint.

In some embodiments, the method further includes a charging cable-connecting step of connecting a charging cable to a port of the retainer. The charging cable-connecting step includes charging a rechargeable battery, which rechargeable battery is the electrical power source.

In some embodiments, the method further includes a determining step of determining whether the electrical-stimulation means is active by observing one or more LEDs of the retainer indicative of active electrical stimulation.

In some embodiments, the method further includes a modulating step of modulating how the electrical power is delivered to the wound dressing by controlling a controller communicatively connected to the catheter-stabilization device.

These and other features of the concepts provided herein will become more apparent to those of skill in the art in view of the accompanying drawings and following description, which describe particular embodiments of such concepts in greater detail.

DRAWINGS

DESCRIPTION

Figure 1:
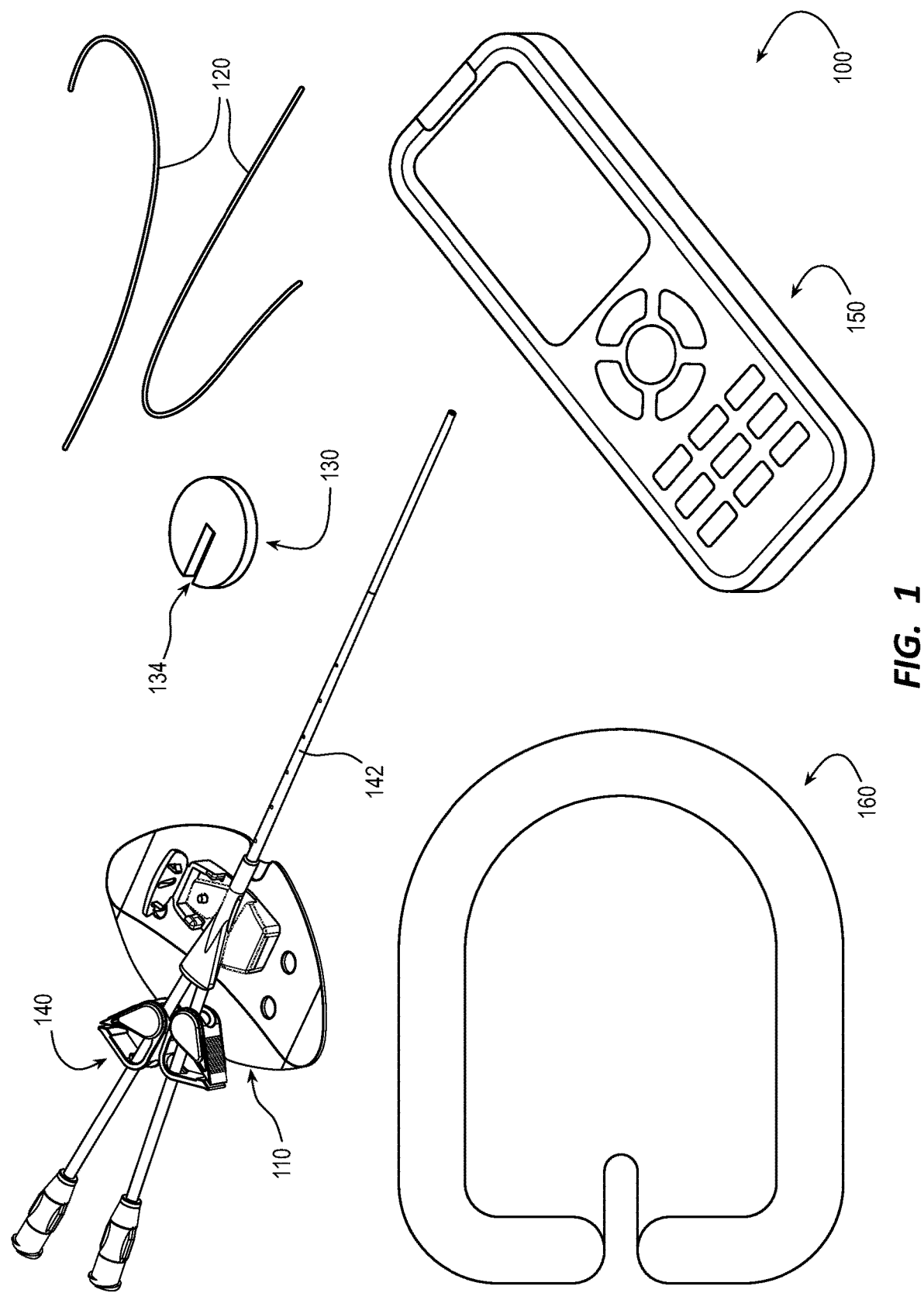
FIG. 1 illustrates a wound-healing system in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

Again, infectious microorganisms such as bacteria can invade a patient's body through a catheter tube disposed in a percutaneous insertion site and subsequently cause an infection (e.g., a deep-tissue infection, sepsis, etc.). While such microorganisms can invade the patient's body through a lumen of the catheter tube, it is more likely the microorganisms colonizing skin of the patient about the insertion site will invade the patient's body. Thus, clinicians routinely suppress the microorganisms about the insertion site by applying an antiseptic such as an alcohol-based chlorhexidine or iodopovidone solution prior to catheterization. However, the microorganisms rapidly grow back about the insertion site during the catheterization, thereby requiring frequent dressing changes in order to reapply the antiseptic and mitigate risk of infection. This leaves ample room for clinician error with respect to inadvertently missing a dressing change, missing or inappropriately applying the antiseptic during a dressing change, or the like.

Disclosed herein are wound-healing systems and methods thereof that address at least the foregoing.

For example, a wound-healing system includes, in some embodiments, a wound dressing, a catheter-stabilization device, and an electrical-stimulation means for applying electrical stimulation to heal or protect at least a wound associated with a percutaneous insertion site of a patient. The electrical stimulation is configured to inhibit growth of microorganisms such as bacteria. Mechanistically, the growth of at least the bacteria is believed to be inhibited by way of disrupting the integrity of bacterial membranes with the electrical stimulation. While inhibiting the growth of the foregoing microorganisms contributes to wound healing, the electrical stimulation is also believed to activate wound-healing cells at the wound, as well as promote migration of the wound-healing cells thereto. In view of such a wound-healing system, the risk of infection by microorganisms such as bacteria is decreased with fewer dressing changes for enhanced wound healing.

Wound-Healing Systems

Figure 2:
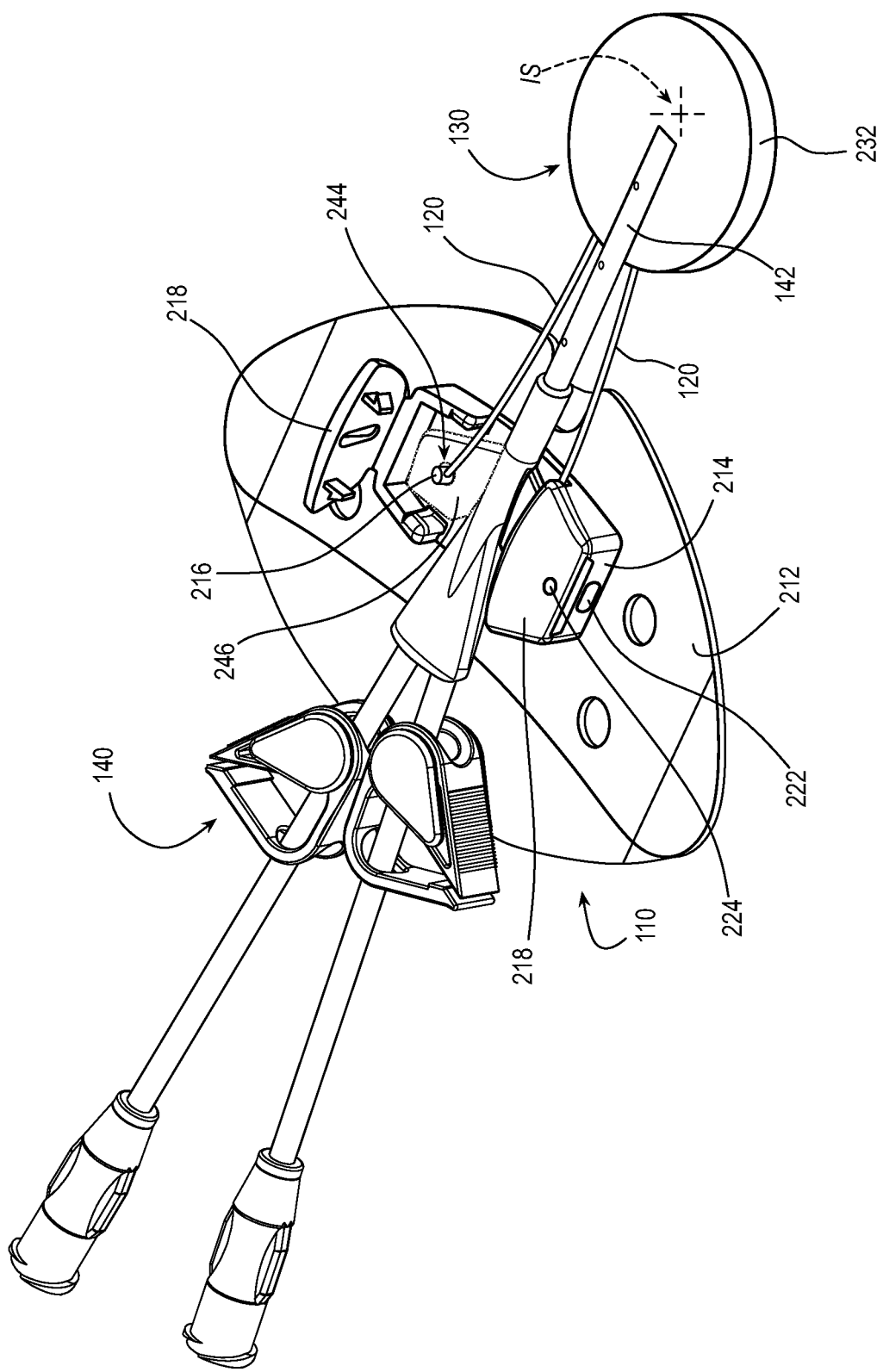
FIG. 2 illustrates a wound-healing system with a first catheter-stabilization device in use on a patient in accordance with some embodiments.
Figure 3:
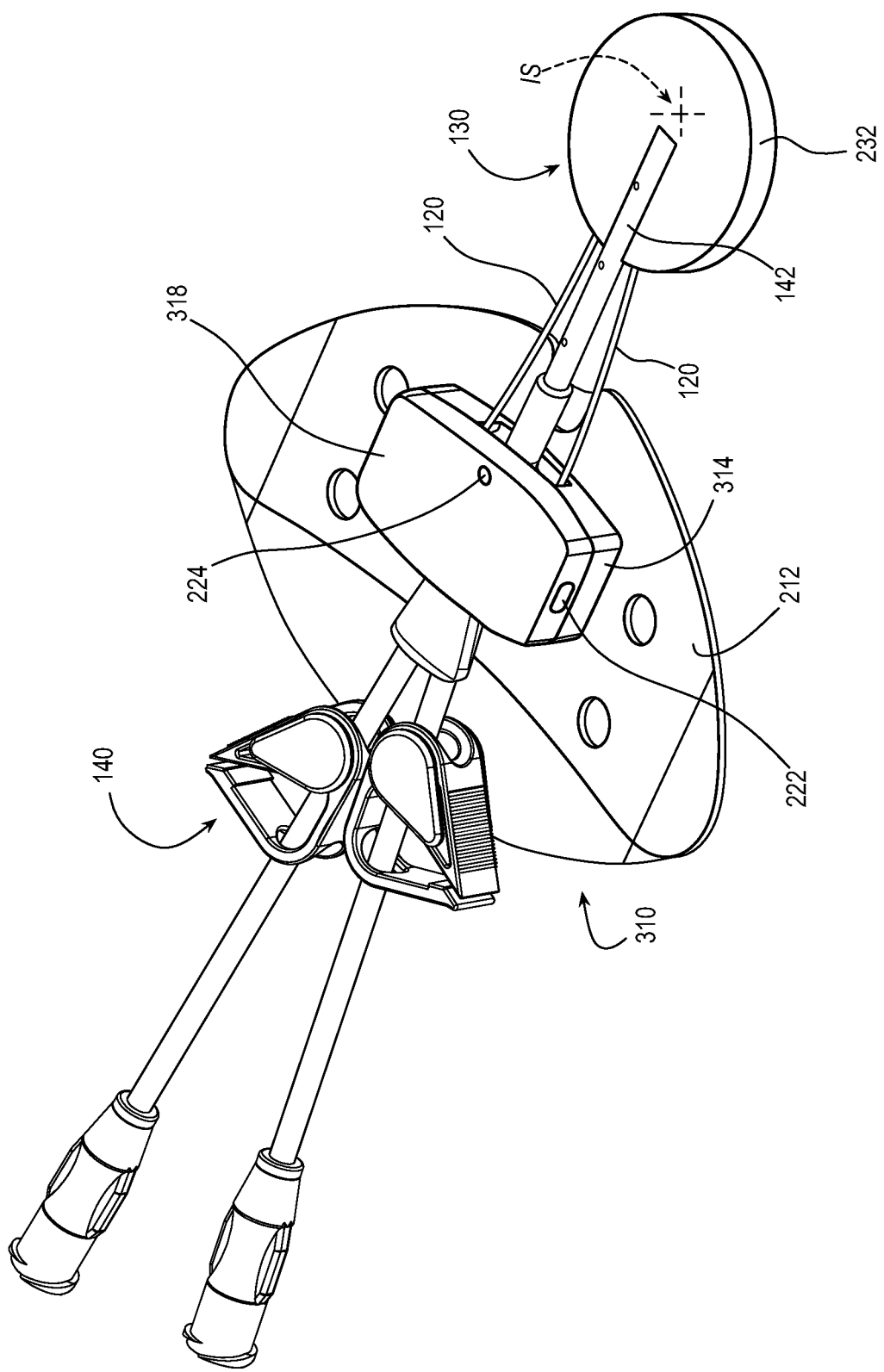
FIG. 3 illustrates a wound-healing system with a second catheter-stabilization device in use on a patient in accordance with some embodiments.

FIG. 1 illustrates a wound-healing system 100 in accordance with some embodiments. FIGS. 2 and 3 illustrate the wound-healing system 100 respectively having a first catheter-stabilization device 110 and a second catheter-stabilization device 310 in use on a patient in accordance with some embodiments. While a catheter assembly 140 is shown in each figure of FIGS. 1-3, an adhesive bandage 160 is shown in FIG. 1, and a controller 150 is shown in FIG. 1, each wound healing-system component of the catheter assembly 140, the adhesive bandage 160, and the controller 150 is an optional component of the wound-healing system 100 in that each of the foregoing components can be separately provided for use in the wound-healing system 100. That said, any one or more components of the catheter assembly 140, the adhesive bandage 160, and the controller 150 can be provided together (e.g., in a kit) with the primary components of the wound-healing system 100 set forth below.

Primary components of the wound-healing system 100 include, but are not limited to, a wound dressing 130, the catheter-stabilization device 110 or 310, and an electrical-stimulation means for applying electrical stimulation to heal or protect at least a wound associated with a percutaneous insertion site of a patient such as the insertion site IS of FIGS. 2 and 3. Each component of the foregoing primary components of the wound-healing system 100 is described in turn below. With respect to the electrical-stimulation means, however, the electrical-stimulation means also includes electrical stimulation-related features of the wound dressing 130 and the catheter-stabilization device 110 or 310. While some of the electrical stimulation-related features of the wound dressing 130 and the catheter-stabilization device 110 or 310 are expressly set forth below as part of the electrical-stimulation means, it should be understood that any feature of the wound dressing 130 or the catheter-stabilization device 110 or 310 in support of providing the electrical stimulation of the wound-healing system 100 can be included as part of the electrical-stimulation means.

The wound dressing 130 is configured as an electrode for placement over and around the wound associated with the insertion site IS of the patient. The wound dressing 130 includes a body 232 having a slot 134 therein configured to accommodate a catheter tube 142 of the catheter assembly 140 while the catheter tube 142 is disposed in the insertion site IS of the patient and the wound dressing 130 is over and around the wound associated therewith.

The body 232 of the wound dressing 130 is electrically conductive or configured to become electrically conductive under certain conditions. The body 232 of the wound dressing 130 includes a matrix of a naturally occurring polymer (e.g., cotton [i.e., cellulose]), a synthetic polymer (e.g., a hydrogel, a polyurethane, etc.), or a composite thereof.

When the body 232 of the wound dressing 130 is electrically conductive, the matrix thereof includes a metal (e.g., copper, silver, etc.), a salt, a conducting polymer, or a conducting allotrope of carbon dispersed therein. For example, the body 232 of the wound dressing 130 can be an electrically conductive hydrogel.

When the body 232 of the wound dressing 130 is configured to become electrically conductive, the body 232 becomes electrically conductive when at least partially saturated with a bodily fluid such as sweat, exudate, blood, or the like, the bodily fluid including, for example, ions for the electrical conductivity. Even when the body 232 of the wound dressing 130 is already electrically conductive, the foregoing bodily fluid can enhance the electrical conductivity.

The body 232 of the wound dressing 130 can include an antimicrobial agent dispersed therethrough, wherein the antimicrobial agent is configured to act synergistically with the electrical stimulation to inhibit the growth of bacteria. The antimicrobial agent can include, but is not limited to, chlorhexidine, silver, or copper. Alternatively or additionally, the body 232 of the wound dressing 130 can include nitric acid, which is reduced to nitric oxide in the body 232 of the wound dressing 130 during the electrical stimulation of the wound. The nitric oxide is subsequently released from the body 232 of the wound dressing 130 as an antimicrobial agent.

The catheter-stabilization device 110 or 310 includes an anchor pad 212 and a retainer 214 or 314 coupled to the anchor pad 212.

The anchor pad 212 is configured to adhere to skin of the patient proximate the insertion site IS as shown in FIGS. 2 and 3. The anchor pad 212 can be a formed of a breathable, non-absorbent tricot polyester or closed cell foam with a hypoallergenic adhesive on a patient-facing side of the anchor pad 212. The retainer 214 or 314 is adhered to a side of the anchor pad 212 opposite the patient-facing side of the anchor pad 212.

The retainer 214 or 314 is configured to stabilize the catheter assembly 140 (e.g., a peripherally inserted central catheter ["PICC"]) while the catheter tube 142 of the catheter assembly 140 is disposed in the insertion site IS as shown in FIGS. 2 and 3. The retainer 214 or 314 can include a suture-wing compartment within a body of the retainer 214 or 314 configured to accept therein a suture wing 246 of the catheter assembly 140. The suture-wing compartment can include posts (e.g., post 216) extending from a bottom of the suture-wing compartment, the posts configured for insertion into suture holes (e.g., suture hole 244) of the suture wing 246 of the catheter assembly 140. The retainer 214 or 314 can be formed of or molded from polyurethane.

The retainer 214 is different than the retainer 314 in that the retainer 214 includes hinged wings 218 coupled to the body of the retainer 214. The hinged wings 218 are configured to outwardly open for inserting the suture wing 246 of the catheter assembly 140 into the suture-wing compartment of the retainer 214. The hinged wings 218 are also configured to inwardly close and snap together with the body of the retainer 214 for locking the suture wing 246 of the catheter assembly 140 in the suture-wing compartment of the retainer 214. The hinged wings 218 include tabs and the body of the retainer 214 includes recesses enabling the hinged wings 218 to snap together with the body of the retainer 214.

The retainer 314 is different than the retainer 214 in that the retainer 314 includes a cover 318 removably or fixedly coupled to the body of the retainer 314. When removably coupled, the cover 318 is configured to snap together with the body of the retainer 314 for locking the suture wing 246 of the catheter assembly 140 in the suture-wing compartment of the retainer 314 after inserting the suture wing 246 therein. Like the retainer 214 and the hinged wings 218 thereof, the cover 318 includes tabs and the body of the retainer 314 includes recesses enabling the cover 318 to snap together with the body of the retainer 314. When fixedly coupled, the cover 318 includes a hinged minor-end portion enabling an unhinged minor-end portion to be lifted away from the body of the retainer 314 for inserting the suture wing 246 of the catheter assembly 140 into the suture-wing compartment of the retainer 314. The unhinged minor-end portion of the cover 318 includes tabs and a corresponding portion of the body of the retainer 314 includes recesses enabling the cover 318 to snap together with the body of the retainer 314 for locking the suture wing 246 of the catheter assembly 140 in the suture-wing compartment of the retainer 314 after inserting the suture wing 246 therein.

The electrical-stimulation means includes an electrical power source and an external circuit between the catheter-stabilization device 110 or 310 and the wound dressing 130 as shown in FIGS. 2 and 3 for applying the electrical stimulation.

While not shown, the electrical power source is a battery (e.g., a microbattery), which can be either a replaceable or rechargeable battery. The battery can be disposed in a battery compartment in the body of the retainer 214 or 314 of the catheter-stabilization device 110 or 310, a wing of the hinged wings 218 of the retainer 214, or the cover 318 of the retainer 314. The battery compartment can be configured to mate with a slide-locking cover over the battery compartment for accessing the battery compartment as needed for replacing the replaceable battery. Alternatively, the battery compartment can be inaccessibly sealed with the rechargeable battery therein to ensure a fuss-free operational state of the catheter-stabilization device 110 or 310. The retainer 214 or 314 can include a charging port 222 electrically coupled to the rechargeable battery for charging the rechargeable battery as needed.

The external circuit includes a pair of electrical leads 120 extending from the catheter-stabilization device 110 or 310, or electrical contacts (e.g., electrical contacts of the posts) thereof electrically coupled to the electrical power source, for connecting with the wound dressing 130. While the electrical leads 120 are shown as being constructed from coated metal wiring, the electrical leads 120 can alternatively be constructed from electrically conductive paint, optionally in a combination with the coated metal wiring. The electrically conductive paint can be painted from the electrical power source, or the electrical contacts of the catheter-stabilization device 110 or 310 electrically coupled therewith, along the catheter tube 142 to less than or equal to about 3 cm from a proximal end of the catheter tube 142 such that the electrically conductive paint is in contact with the wound dressing 130.

The electrical-stimulation means can also include an integrated circuit disposed in the body of the retainer 214 or 314 of the catheter-stabilization device 110 or 310, a wing of the hinged wings 218 of the retainer 214, or the cover 318 of the retainer 314. The integrated circuit includes at least a power circuit and a control circuit. While the wound-healing system 100 is in use, the power circuit is coupled to the external circuit. The power circuit is configured to convey electrical power from the electrical power source to the wound dressing 130 by way of the external circuit. The control circuit is configured to modulate how the electrical power is delivered to the wound dressing 130 through the power circuit and the external circuit.

The integrated circuit can be configured to modulate the electrical power in a number of different ways. For example, the integrated circuit can be configured to modulate the electrical power such that a low-intensity current between about 200 and 1000 mA is continuously delivered to the wound dressing 130 for more than 1 s at a time. Such a current can have a particular polarity. It is believed application of such a low-intensity current activates wound-healing cells at the wound, as well as promotes migration of the wound-healing cells thereto. The integrated circuit can also be configured to modulate the electrical power such that a high-voltage current between about 50 and 150 V is delivered to the wound dressing 130 in 1-ms pulses or pulses less than 1 ms. Such a current can have an alternating polarity or a particular polarity. It is believed application of such a high-voltage current inhibits the growth of bacteria by way of disrupting the integrity of bacterial membranes with the electrical stimulation.

The integrated circuit can include biofeedback logic configured to detect changes in impedance through the skin of the patient or the wound dressing 130. The biofeedback logic can also be configured to modulate how the electrical power is delivered to the wound dressing 130 in accordance with the changes in impedance. In addition to modulating how the electrical power is delivered to the wound dressing 130, the biofeedback logic can be configured to detect excessive bleeding by way of the changes in impedance.

While not necessarily part of the electrical-stimulation means, the body of the retainer 214 or 314 of the catheter-stabilization device 110 or 310, a wing of the hinged wings 218 of the retainer 214, or the cover 318 of the retainer 314 can include one or more LEDs 224 configured to indicate when the electrical-stimulation means is active, what mode the electrical-stimulation means is using, when the battery needs to be recharged or replaced, etc.

The wound-healing system 100 can further include the controller 150, which is representative of a bedside controller, a handheld controller, or even a smartphone having a communications module configured to communicate over Wi-Fi, Bluetooth®, or the like with a communications module in the retainer 214 or 314 of the catheter-stabilization device 110 or 310. The controller 150 is configured to allow a user thereof to modulate how the electrical power is delivered to the wound dressing 130. For example, the controller 150 can be configured to freely allow the user to adjust frequency, duration, voltage, or polarity of the electrical power delivered to the wound dressing 130, which can be useful in inhibiting growth of bacteria or optimizing one or more stages of wound healing. Alternatively or additionally, the controller 150 can be configured with one or more programs, settings, or modes to automatically adjust the frequency, duration, voltage, or polarity of the electrical power delivered to the wound dressing 130.

The wound-healing system 100 can further includes the adhesive bandage 160 for placement over a combination of the wound dressing 130, the catheter-stabilization device 110 or 310, and the catheter assembly 140. The adhesive bandage 160 includes a patient-facing side having a hypoallergenic adhesive configured to adhere the combination of the wound dressing 130, the catheter-stabilization device 110 or 310, and the catheter assembly 140 to the patient for further stabilization. The adhesive bandage 160 can include a transparent window with reinforced edges of non-absorbent tricot polyester such that the combination of the wound dressing 130, the catheter-stabilization device 110 or 310, and the catheter assembly 140 can be viewed through the transparent window for monitoring the wound-healing system 100. Notably, if the electrical leads 120 of the external circuit of the electrical-stimulation means are constructed from the electrically conductive paint, the adhesive bandage 160 can protect the electrical leads 120 from wear by limiting exposure of the electrical leads 120.

Methods

Methods of the wound-healing system 100 include at least a method of using the wound-healing system 100. If the catheter assembly 140 is provided with the wound-healing system 100, using the wound-healing system 100 can include an inserting step of inserting the catheter tube 142 of the catheter assembly 140 into a percutaneous insertion site such as the insertion site IS shown in FIGS. 2 and 3. The method can also include a stabilizing step of stabilizing the catheter assembly 140 in the retainer 214 or 314 of the catheter-stabilization device 110 or 310 while the catheter tube 142 of the catheter assembly 140 is disposed in the insertion site IS.

The method of using the wound-healing system 100 generally includes a wound dressing-applying step of applying the wound dressing 130 around a wound associated with the insertion site IS. The method also includes an adhering step of adhering the anchor pad 212 of the catheter-stabilization device 110 or 310 to skin of the patient proximate the insertion site IS. The method also includes an electrical lead-connecting step of connecting the electrical leads 120 from the catheter-stabilization device 110 or 310 to the wound dressing 130 to form the external circuit for applying the electrical stimulation. The electrical lead-connecting step can include painting the electrical leads 120 on the catheter assembly 140 with electrically conductive paint. The method also includes an electrical stimulation-applying step of applying electrical stimulation with the electrical-stimulation means therefor to heal the wound.

The method can further include a determining step of determining whether or not the electrical-stimulation means is active by observing the one or more LEDs 224 of the retainer 214 or 314 indicative of active electrical stimulation.

The method can further include a modulating step of modulating how the electrical power is delivered to the wound dressing 130 by controlling the controller 150 while it is communicatively connected to the catheter-stabilization device 110 or 310.

The method can further include another determining step of determining whether or not the rechargeable battery needs charging. If so, the method can further include a charging cable-connecting step of connecting the charging cable to the charging port 222 of the retainer 214 or 314 of the catheter-stabilization device 110 or 310. The charging cable-connecting step can include charging the rechargeable battery.

The method further can further include a placing step of placing the adhesive bandage 160 over a combination of the wound dressing 130, the catheter-stabilization device 110 or 310, and the catheter assembly 140 to adhere the foregoing combination to the patient for further stabilization.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A wound-healing system, comprising:
   a wound dressing configured as an electrode for placement around a wound associated with a percutaneous insertion site of a patient;
   a catheter-stabilization device including:
   an anchor pad configured to adhere to skin of the patient proximate the insertion site, and
   a retainer coupled to the anchor pad configured to stabilize a catheter assembly while a catheter tube of the catheter assembly is disposed in the insertion site; and
   an electrical-stimulation means for applying electrical stimulation to heal or protect the wound, the electrical-stimulation means including:
   an electrical power source, and
   an external circuit between the catheter-stabilization device and the wound dressing for applying the electrical stimulation.

2. The wound-healing system of claim 1, further comprising an adhesive bandage configured for placement over a combination of the wound dressing, the catheter-stabilization device, and the catheter assembly to adhere the combination to the patient for further stabilization.

3. The wound-healing system of claim 1, wherein the wound dressing includes an electrically conductive body, the body including a matrix of a naturally occurring polymer, a synthetic polymer, or a composite thereof having a metal, a salt, a conducting polymer, or a conducting allotrope of carbon dispersed therein.

4. The wound-healing system of claim 3, wherein the body of the wound dressing includes an electrically conductive hydrogel.

5. The wound-healing system of claim 1, wherein the wound dressing includes a body, the body including a matrix of a naturally occurring polymer, a synthetic polymer, or a composite thereof configured to become electrically conductive when at least partially saturated with a bodily fluid.

6. The wound-healing system of claim 3, wherein the wound dressing includes an antimicrobial agent.

7. The wound-healing system of claim 1, wherein the external circuit includes a pair of electrical leads extending from the catheter-stabilization device for connecting with the wound dressing, the pair of electrical leads constructed from coated metal wiring, electrically conductive paint, or a combination thereof.

8. The wound-healing system of claim 1, wherein the electrical-stimulation means includes an integrated circuit disposed in a body of the retainer, a wing of the retainer, or a cover of the retainer for locking a portion of the catheter assembly in the retainer, the integrated circuit including at least a power circuit coupled to the external circuit configured to convey electrical power from the electrical power source to the wound dressing and a control circuit configured to modulate how the electrical power is delivered to the wound dressing.

9. The wound-healing system of claim 8, wherein the integrated circuit is configured to modulate the electrical power such that a low-intensity current between about 200 and 1000 mA having a particular polarity is continuously delivered to the wound dressing for more than 1 s at a time.

10. The wound-healing system of claim 8, wherein the integrated circuit is configured to modulate the electrical power such that a high-voltage current between about 50 and 150 V having an alternating polarity or a particular polarity is delivered to the wound dressing in 1-ms pulses.

11. The wound-healing system of claim 8, wherein the integrated circuit includes biofeedback logic configured to detect changes in impedance through the skin of the patient or the wound dressing and modulate how the electrical power is delivered to the wound dressing.

12. The wound-healing system of claim 1, wherein the electrical power source is a battery, the battery being either rechargeable or replaceable.

13. The wound-healing system of claim 12, wherein the battery is rechargeable, the retainer including a port for charging the battery.

14. The wound-healing system of claim 1, wherein the retainer includes one or more light-emitting diodes ("LEDs") configured to indicate when the electrical-stimulation means is active.

15. The wound-healing system of claim 1, further comprising a controller configured to communicatively connect to the catheter-stabilization device and allow a user thereof to modulate how electrical power is delivered to the wound dressing.

16. A wound-healing system, comprising:
a wound dressing configured as an electrode for placement around a wound associated with a percutaneous insertion site of a patient;
a catheter-stabilization device including:
an anchor pad configured to adhere to skin of the patient proximate the insertion site, and
a retainer coupled to the anchor pad configured to stabilize a catheter assembly while a catheter tube of the catheter assembly is disposed in the insertion site;
an electrical-stimulation means for applying electrical stimulation to heal or protect the wound, the electrical-stimulation means including:
an electrical power source,
an external circuit between the catheter-stabilization device and the wound dressing for applying the electrical stimulation, the external circuit including a pair of electrical leads extending from the catheter-stabilization device for connecting with the wound dressing, and
an integrated circuit disposed in a body of the retainer or a wing or cover of the retainer for locking a portion of the catheter assembly in the retainer, the integrated circuit including at least a power circuit coupled to the external circuit configured to convey electrical power from the electrical power source to the wound dressing and a control circuit configured to modulate how the electrical power is delivered to the wound dressing; and
an adhesive bandage configured for placement over a combination of the wound dressing, the catheter-stabilization device, and the catheter assembly to adhere the combination to the patient for further stabilization.

17. A method of a wound-healing system, comprising:
applying a wound dressing around a wound associated with a percutaneous insertion site of a patient, the wound dressing configured as an electrode;
adhering an anchor pad of a catheter-stabilization device to skin of the patient proximate the insertion site;
stabilizing a catheter assembly in a retainer of the catheter-stabilization device, the retainer coupled to the anchor pad; and
applying electrical stimulation with an electrical-stimulation means therefor to heal or protect the wound, the electrical-stimulation means including an electrical power source and an external circuit between the catheter-stabilization device and the wound dressing for applying the electrical stimulation.

18. The method of claim 17, further comprising inserting a catheter tube of the catheter assembly into the insertion site before stabilizing the catheter assembly in a retainer of the catheter-stabilization device.

19. The method of claim 17, further comprising placing an adhesive bandage over a combination of the wound dressing, the catheter-stabilization device, and the catheter assembly to adhere the combination to the patient for further stabilization.

20. The method of claim 17, further comprising connecting a pair of electrical leads from the catheter-stabilization device to the wound dressing to form an external circuit for applying the electrical stimulation.

21. The method of claim 20, wherein connecting the pair of electrical leads from the catheter-stabilization device to the wound dressing includes painting the pair of electrical leads on the catheter assembly with electrically conductive paint.

22. The method of claim 17, further comprising connecting a charging cable to a port of the retainer and charging a rechargeable battery, the rechargeable battery being the electrical power source.

23. The method of claim 17, further comprising determining whether the electrical-stimulation means is active by observing one or more light-emitting diodes ("LEDs") of the retainer indicative of active electrical stimulation.

24. The method of claim 17, further comprising modulating how electrical power is delivered to the wound dressing by controlling a controller communicatively connected to the catheter-stabilization device.

* * * * *